US010898621B2

(12) United States Patent
Chen et al.

(10) Patent No.: US 10,898,621 B2
(45) Date of Patent: *Jan. 26, 2021

(54) MULTI-ORIENTATION CANISTER FOR USE WITH A REDUCED PRESSURE TREATMENT SYSTEM

(71) Applicant: KCI Licensing, Inc., San Antonio, TX (US)

(72) Inventors: Fernando T. Chen, San Antonio, TX (US); Kevin H. Dai, Dugan, NC (US); Stephen C. Yeadon, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 343 days.

This patent is subject to a terminal disclaimer.

(21) Appl. No.: 15/971,873

(22) Filed: May 4, 2018

(65) Prior Publication Data
US 2018/0250448 A1    Sep. 6, 2018

Related U.S. Application Data

(60) Continuation of application No. 14/271,991, filed on May 7, 2014, now Pat. No. 9,987,401, which is a (Continued)

(51) Int. Cl.
    *A61M 1/00*    (2006.01)
(52) U.S. Cl.
    CPC ........ *A61M 1/0001* (2013.01); *A61M 1/0088* (2013.01); *A61M 1/0096* (2014.02); *A61M 2205/21* (2013.01); *A61M 2205/75* (2013.01)

(58) Field of Classification Search
    CPC .............. A61M 1/0001; A61M 1/0003; A61M 1/0017; A61M 1/0088; A61M 1/0096;
    (Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion for corresponding PCT/US2012/025962, dated Nov. 30, 2012.
(Continued)

*Primary Examiner* — Catherine L Anderson (57) ABSTRACT

Systems and methods for reduced pressure tissue treatments, including a multi-orientation canister. The canister includes an inlet for receiving fluids from a tissue site, and a main chamber in fluid communication with the inlet for receiving fluids from the inlet. The canister includes a filter chamber separated from the main chamber by one or more filter chamber walls. The one or more filter chamber walls includes a primary hole having a first diameter and a secondary hole having a second diameter smaller than the first diameter. The primary hole provides a first path of fluid communication between the filter chamber and the main chamber. The canister includes an outlet for providing fluid communication between the filter chamber and a reduced pressure source.

18 Claims, 6 Drawing Sheets

Related U.S. Application Data division of application No. 13/401,433, filed on Feb. 21, 2012, now Pat. No. 8,758,315.

(58) Field of Classification Search
CPC ............ A61M 1/0098; A61M 2205/21; A61M 2205/75
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,631,654 A | 1/1972 | Riely et al. | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,516,973 A | 5/1985 | Telang | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,886,492 A | 12/1989 | Brooke | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,957,492 A | 9/1990 | McVay | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,779,649 A | 7/1998 | Herbert | |
| 6,071,267 A | 6/2000 | Zamierowski | |
| 6,135,116 A | 10/2000 | Vogel et al. | |
| 6,210,383 B1 | 4/2001 | Want et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,216,651 B2 | 5/2007 | Argenta et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 9,987,401 B2 * | 6/2018 | Chen | A61M 1/0088 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0030304 A1 | 2/2004 | Hunt et al. | |
| 2007/0016152 A1 | 1/2007 | Karpowicz et al. | |
| 2009/0221990 A1 | 9/2009 | Jaeb et al. | |
| 2009/0299307 A1 | 12/2009 | Barta et al. | |
| 2009/0306610 A1 | 12/2009 | Van Den Heuvel et al. | |
| 2009/0306630 A1 | 12/2009 | Locke et al. | |
| 2011/0060300 A1 | 3/2011 | Weig et al. | |
| 2011/0152799 A1 | 6/2011 | Kevin et al. | |
| 2011/0257612 A1 | 10/2011 | Locke et al. | |
| 2012/0046624 A1 | 2/2012 | Locke et al. | |
| 2014/0163491 A1 | 6/2014 | Schuessler et al. | |
| 2015/0080788 A1 | 3/2015 | Blott et al. | |

FOREIGN PATENT DOCUMENTS

| | | | |
|---|---|---|---|
| AU | 755496 B2 | 12/2002 | |
| CA | 2005436 A1 | 6/1990 | |

(56) References Cited

FOREIGN PATENT DOCUMENTS

| | | |
|---|---|---|
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 1234589 A1 | 8/2002 |
| EP | 1837045 A1 | 9/2007 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2009089016 A1 | 7/2009 |
| WO | 2009111341 A2 | 9/2009 |
| WO | 2009149250 A1 | 12/2009 |

OTHER PUBLICATIONS

Chinese First Office Action for Corresponding Application No. 2017101697261, dated Nov. 8, 2018.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson,"An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its (56) References Cited

OTHER PUBLICATIONS

Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

MULTI-ORIENTATION CANISTER FOR USE WITH A REDUCED PRESSURE TREATMENT SYSTEM

CROSS-REFERENCE TO RELATED APPLICATION

This application is a continuation of U.S. patent application Ser. No. 14/271,991, filed May 7, 2014, which is a divisional of U.S. patent application Ser. No. 13/401,433 entitled "Multi-Orientation Canister For Use With A Reduced Pressure Treatment System", filed Feb. 21, 2012, each of which are hereby incorporated by reference for all purposes.

BACKGROUND

1. Field of the Invention

The present invention relates generally to reduced pressure treatment systems and more particularly to a multi-orientation canister for use with a reduced pressure treatment system.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and microdeformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment. Fluids drawn from the tissue site are often collected in a canister.

SUMMARY

The problems presented by existing reduced pressure treatment systems are solved by the systems and methods of the illustrative embodiments described herein. In one illustrative embodiment, a multi-orientation canister for use in a reduced pressure tissue treatment includes an inlet adapted to be fluidly connected with a tissue site, the inlet being capable of receiving fluids from the tissue site, and a main chamber in fluid communication with the inlet for receiving fluids from the inlet. The multi-orientation canister further includes a filter chamber separated from the main chamber by one or more filter chamber walls. The one or more filter chamber walls includes a primary hole having a first diameter and a secondary hole having a second diameter smaller than the first diameter. The primary hole is positioned through the one or more filter chamber walls for providing a first path of fluid communication between the filter chamber and the main chamber. The multi-orientation canister further includes an outlet for providing fluid communication with the filter chamber such that the outlet is adapted to be fluidly connected to a reduced pressure source.

In another illustrative embodiment, a canister for use in a reduced pressure tissue treatment includes one or more canister walls arranged to create an enclosure with a main chamber and a filter chamber positioned within the enclosure. The main chamber may collect exudate received by a tissue site. The filter chamber has a first filter chamber wall and a second filter chamber wall for partitioning the filter chamber from the main chamber. A first aperture extends through the first filter chamber wall spaced apart from the one or more canister walls. A second aperture smaller than the first aperture extends through the second filter chamber wall.

In yet another illustrative embodiment, a canister for use in a reduced pressure tissue treatment includes a main chamber having an inlet adapted to receive liquid from a tissue site and a filter chamber isolated from the main chamber by one or more walls. The filter chamber has an outlet adapted to be fluidly coupled to a reduced pressure source. A first aperture and a second aperture extend through the one or more walls. The first aperture is configured to provide fluid communication between the main chamber and the filter chamber until the first aperture is occluded by the liquid. Upon occlusion of the first aperture by the liquid, the second aperture is configured to provide fluid communication between the main chamber and the filter chamber.

In another illustrative embodiment, a liquid-collection canister includes a first and second chamber fluidly isolated by one or more walls and a plurality of apertures positioned in the one or more walls to provide fluid communication between the first and second chambers. The plurality of apertures are not covered by a membrane.

In another illustrative embodiment, a canister for use in a reduced pressure tissue treatment includes a main chamber having an inlet adapted to receive liquid from a tissue site and a filter chamber isolated from the main chamber by one or more walls. The filter chamber includes an outlet adapted to be fluidly coupled to a reduced pressure source. The canister further includes a filter positioned within the filter chamber as well as a first aperture and a second aperture extending through the one or more walls. The first and second apertures are sized to prevent fluid, upon entrance into the main chamber, from incidentally contacting the filter.

In yet another illustrative embodiment, a reduced pressure delivery system for applying a reduced pressure tissue treatment to a tissue site includes a multi-orientation canister. The multi-orientation canister includes one or more canister walls arranged to create an enclosure, a main chamber positioned within the enclosure for receiving exudate from a tissue site, and a filter chamber positioned within the enclosure. The filter chamber has a first filter chamber wall and a second filter chamber wall for partitioning the filter chamber from the main chamber. A first aperture extends through the first filter chamber wall spaced apart from the one or more canister walls, and a second aperture smaller than the first aperture extends through the second filter chamber wall. The system further includes a reduced pressure source fluidly connected to the multi-orientation canister for applying reduced pressure to the tissue site, a manifold positioned adjacent the tissue site, and a conduit fluidly connected between the main chamber and the manifold for delivering fluids from the tissue site to the main chamber.

In another illustrative embodiment, a reduced pressure delivery system for applying a reduced pressure tissue treatment to a tissue site includes a liquid-collection canister. The liquid-collection canister includes a first and second chamber fluidly isolated by one or more walls, and a plurality of apertures positioned in the one or more walls to provide fluid communication between the first and second chambers. The plurality of apertures are not covered by a membrane. The system further includes a reduced pressure source for applying reduced pressure to the tissue site, a manifold positioned adjacent the tissue site, and a conduit fluidly connected between the main chamber and the manifold for delivering fluids from the tissue site to the main chamber.

In another illustrative embodiment, a method for emptying fluids from a filter chamber positioned in a canister used in reduced pressure tissue treatment includes the steps of receiving fluids into a main chamber of the canister and rotating the canister into a first position to cause fluids in the main chamber to flow into the filter chamber through either a first aperture or a second aperture. The first aperture is larger than the second aperture, and the first aperture is located in a first plane substantially perpendicular to a second plane of which the second aperture is located. The method further includes the step of rotating the canister into a second position to cause fluids in the filter chamber to flow back into the main chamber through the first aperture.

In yet another illustrative embodiment, a method for extending the use of a filter positioned in a multi-orientation canister used in reduced pressure tissue treatment includes the step of receiving fluids into a main chamber of the multi-orientation canister such that the fluids react with a gelling agent to create a gel. The method further includes applying reduced pressure to the main chamber via a first aperture positioned in a partition that separates the main chamber from a filter chamber until a fluid or gel level in the main chamber covers the first aperture thereby causing a temporary blockage of the first aperture. The method further includes the step of responsive to the first aperture becoming temporarily blocked, continuing to apply reduced pressure to the main chamber via a second aperture positioned in the partition until the fluid or gel level in the main chamber covers the second aperture. The first aperture is a distance, D, from the second aperture. The method further includes the step of responsive to the fluid or gel level covering the second aperture, continuing to apply reduced pressure to the main chamber through the first aperture causing the gel in the main chamber to pulled into the filter chamber until both the main chamber and the filter chamber are substantially full of gel.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Reduced pressure treatment systems often use canisters for collecting exudate, including liquids and other fluids, received from a tissue site undergoing reduced pressure tissue treatment. Exudate collected within the canister may move within the canister by way of splashing or sloshing for a number of reasons. For example, when the exudate enters the canister, they may splash or foam within the canister enclosure. Likewise, once the exudate has entered the canister, the exudate may slosh due to canister movement. In some circumstances, the canister is worn by a patient and may be subject to orientation changes as the patient bends over or moves in general. The movement of the exudate within the canister may cause the exudate to come into contact with a filter used to protect the reduced pressure source from contamination.

The filter may be positioned within the canister to block unwanted liquids from contaminating the reduced pressure source. When wound exudate contacts the filter, even if the contact is brief, such as when the filter is splashed by exudate or the canister undergoes a brief orientation change due to patient movement, the exudate may leave a protein film or deposit on the filter. The protein deposits can build-up on the filter as the filter is subject to repeated and prolonged contact with exudate, compromising the filter's ability to allow air flow between the canister and the reduced pressure source.

A blocked or compromised filter can create at least two problems. The first problem is that restricting air flow between the canister and the reduced pressure source causes air flow restriction at the wound site. Restricting the ability of the reduced pressure system from drawing air from the tissue site results in an inability to maintain reduced pressure at the tissue site. The other problem is that when the air flow between the canister and the reduced pressure source is restricted, an alarm may sound indicating that the canister is full and needs to be emptied or changed, when, in fact, the canister is not full. Reduced pressure therapy systems may have an alarm indicating that a canister is full based on reduced pressure no longer being supplied to the tissue site at a desired treatment level. Since false canister-full alarms are both wasteful in time and resources, it would be beneficial for a canister that is configured to be worn on a patient's body, and is therefore, subject to orientation changes, to have a means for protecting the filter from contacting exudate until the canister is truly full of exudate. Additionally, it would be beneficial for the canister to be able to drain unwanted exudate away from the filter in the event the exudate contacts the filter before the canister is full.

Figure 1:
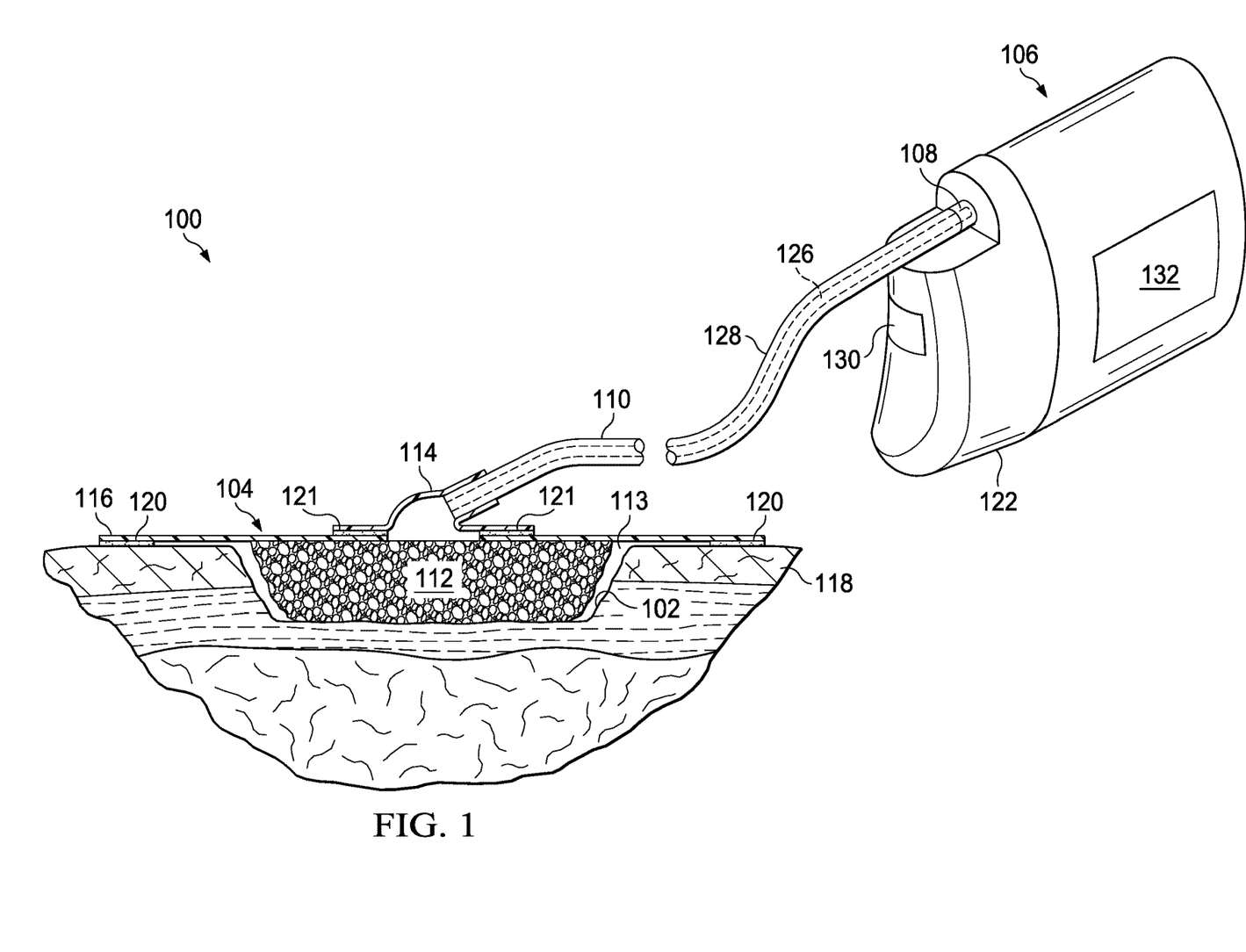
FIG. 1 illustrates a perspective view, with a portion shown in cross-section, of a reduced pressure treatment system, including a multi-orientation canister.
Figure 2:
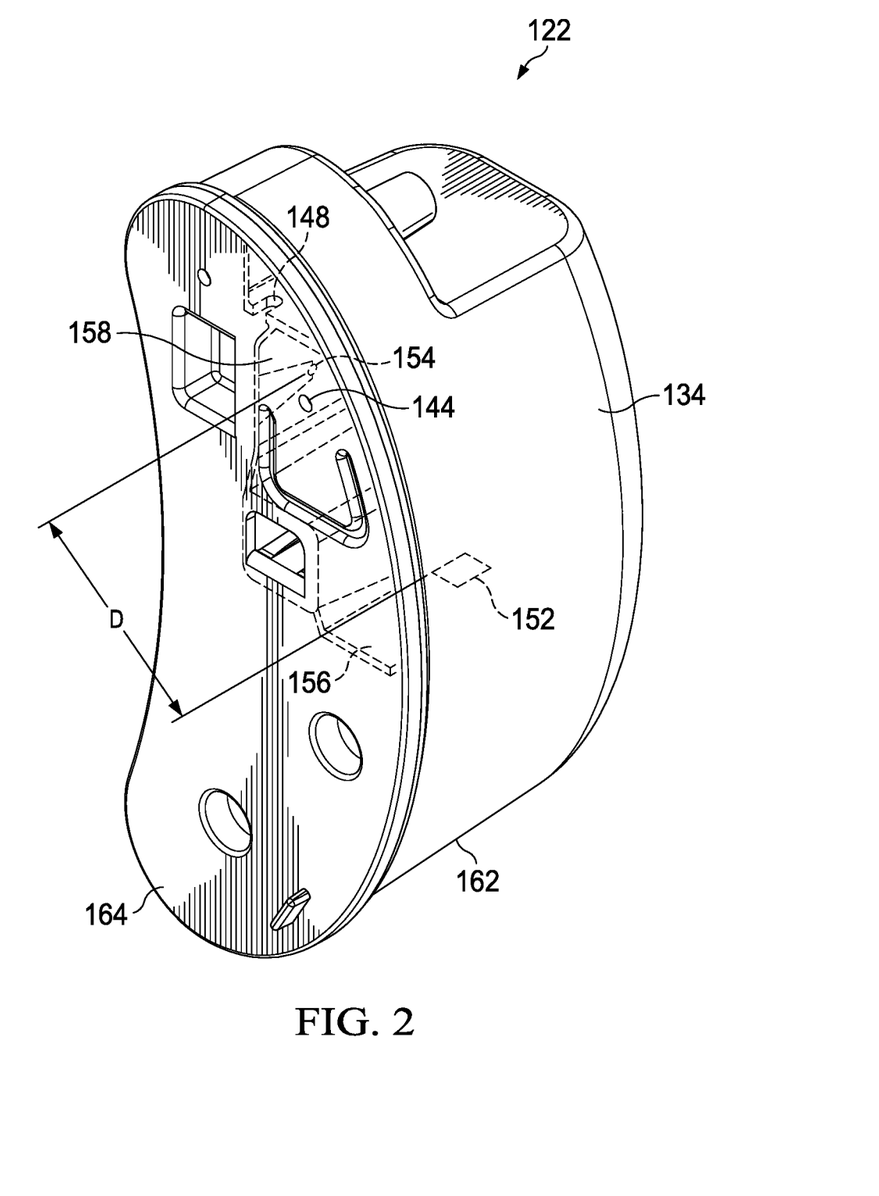
FIG. 2 illustrates a perspective view of one illustrative embodiment of a multi-orientation canister, with a portion shown with hidden lines, for use with the reduced pressure treatment system illustrated in FIG. 1.
Figure 3:
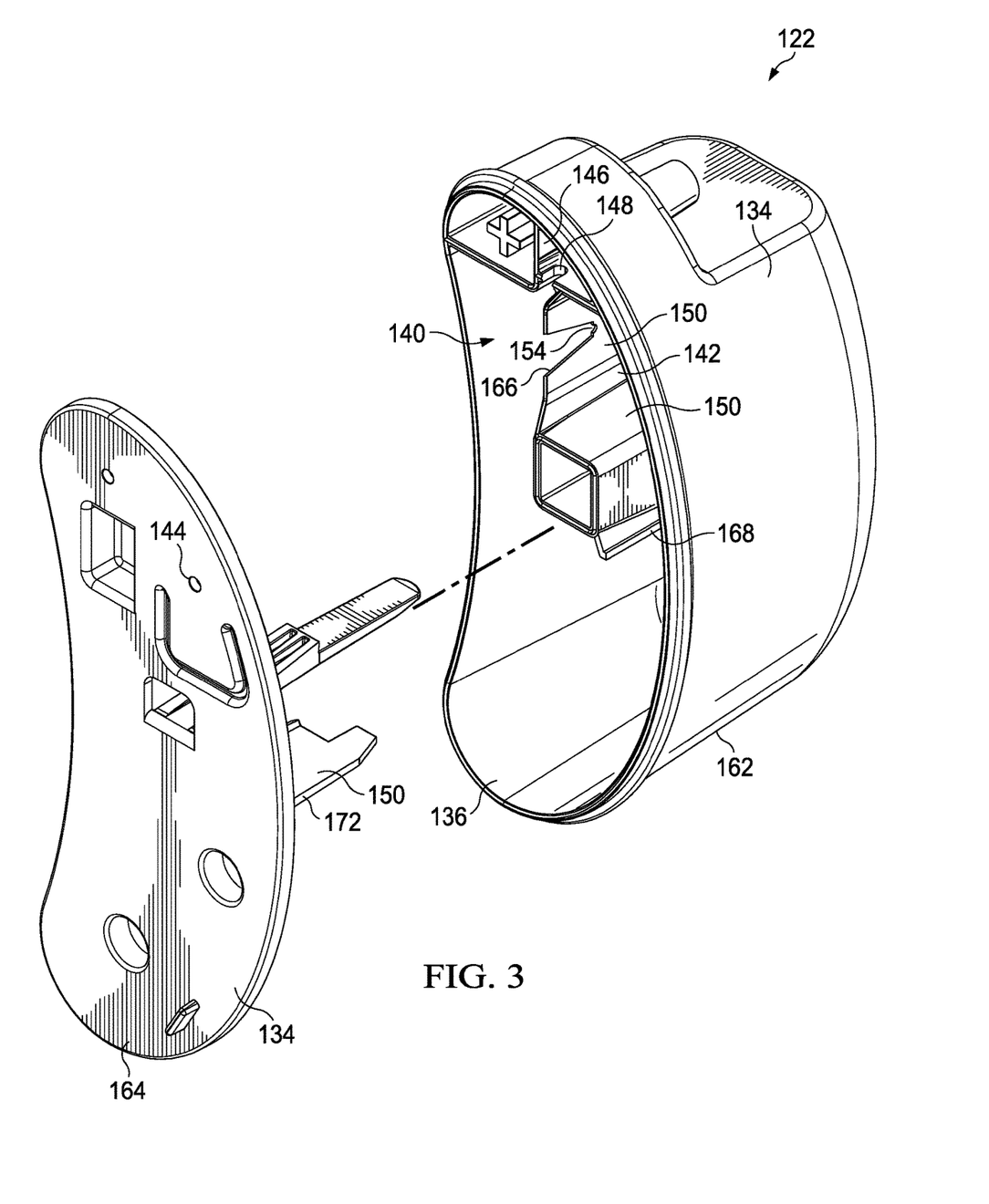
FIG. 3 illustrates a perspective, exploded view of the multi-orientation canister illustrated in FIG. 2.
Figure 4:
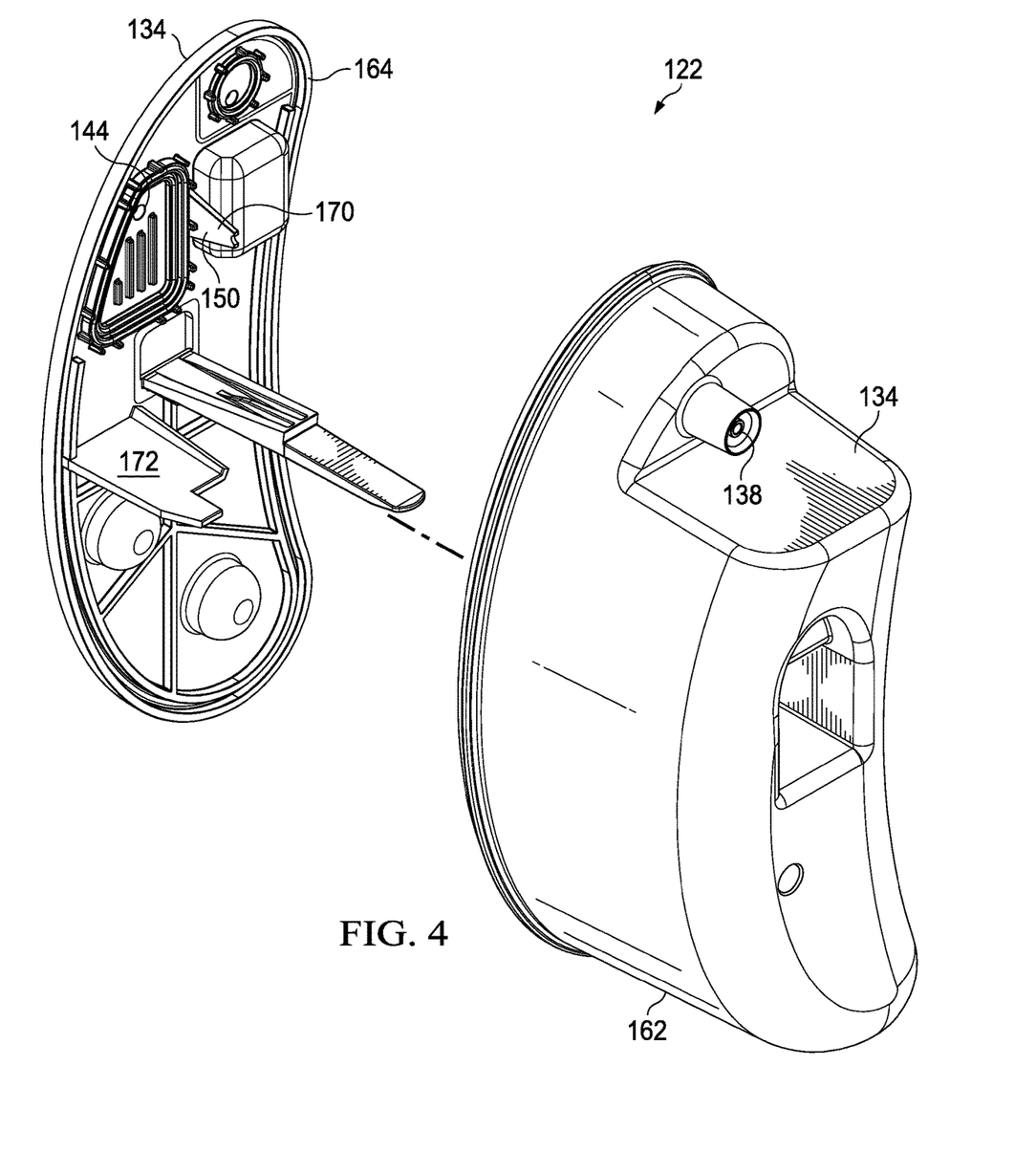
FIG. 4 illustrates another perspective, exploded view of the multi-orientation canister illustrated in FIG. 2.
Figure 5:
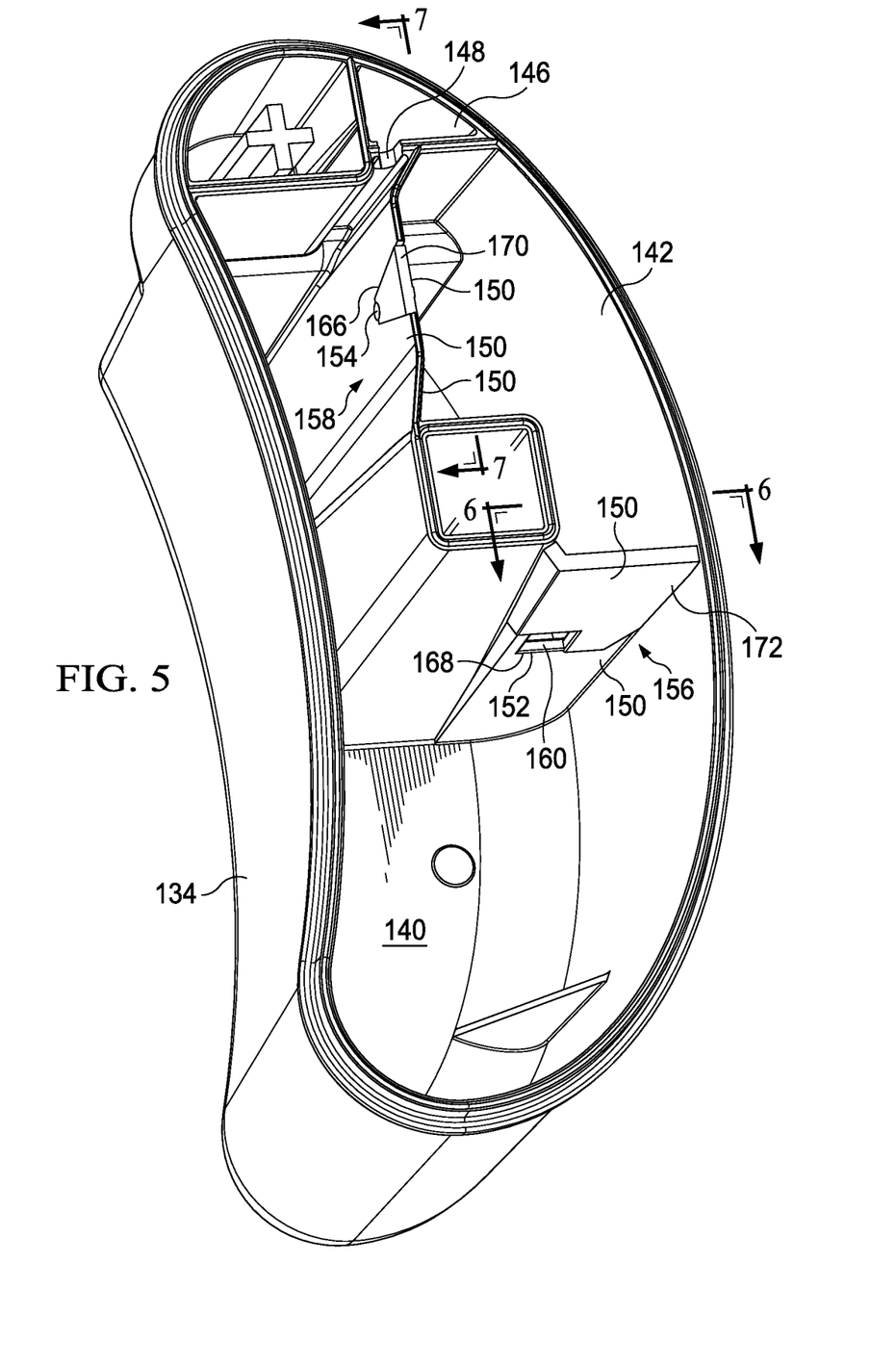
FIG. 5 illustrates a perspective view of the multi-orientation canister of FIG. 2 with a back face plate and the attached clip removed.
Figure 6:
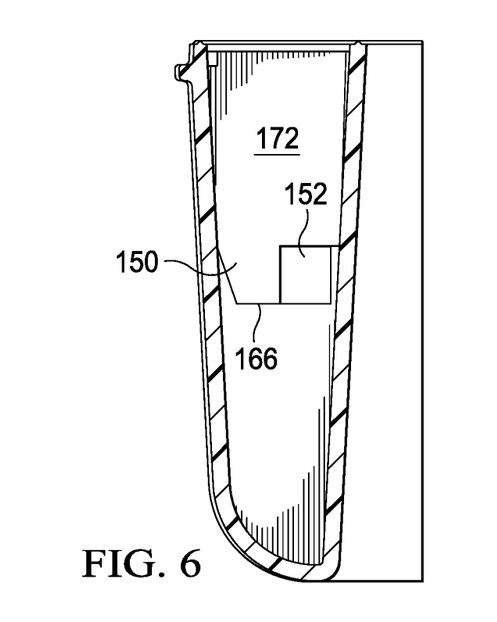
FIG. 6 illustrates a sectional view of the multi-orientation canister of FIG. 5 taken along line 6-6.
Figure 7:
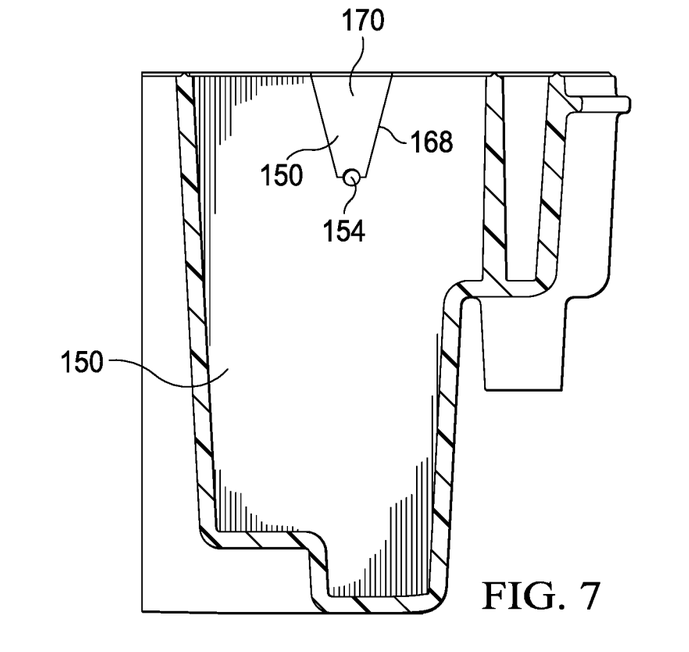
FIG. 7 illustrates a sectional view of the multi-orientation canister of FIG. 5 taken along line 7-7.

Referring to FIG. 1, an illustrative embodiment of a reduced pressure treatment system 100 for treating a tissue site 102 on a patient includes a dressing 104 placed proximate the tissue site 102, and a reduced pressure treatment unit 106 fluidly coupled to the dressing 104 via a reduced pressure connector 108 and a conduit 110. As used herein, the term "tissue site" may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 104 may include a manifold 112 placed proximate the tissue site 102, a reduced pressure interface 114 fluidly coupled to the manifold 112, and a drape 116. The drape 116 may be placed over the manifold 112 to secure the manifold 112 at the tissue site 102 and to create a fluidly sealed space 113 that is located beneath the drape and that is at least partially occupied by the manifold 112. In one embodiment, the drape 116 extends beyond a perimeter of the tissue site 102 and is placed over a patient's epidermis 118 to create the fluidly sealed space 113 between the drape 116 and the epidermis 118. The drape 116 may include an adhesive 120 or bonding agent to secure the drape 116 to the epidermis 118. In one embodiment, the adhesive 120 may be used to create a seal between the drape 116 and the epidermis 118 to prevent leakage of reduced pressure from the tissue site 102. In another embodiment, a seal layer (not shown) such as, for example, a hydrogel or other material may be disposed between the drape 116 and the epidermis 118 to augment or substitute for the sealing properties of the adhesive 120. As used herein, "fluid seal" means a seal adequate to maintain reduced pressure at a desired site given the particular reduced pressure source involved.

The term manifold generally refers to a substance or structure that is provided to assist in applying reduced pressure to, delivering fluids to, or removing fluids from the tissue site 102. The manifold 112 typically includes a plurality of flow channels or pathways that distribute fluids provided to and removed from the tissue site around the manifold 112. In one illustrative embodiment, the flow channels or pathways are interconnected to improve distribution of fluids provided or removed from the tissue site 102. Examples of manifolds 112 may include, for example, without limitation, devices that have structural elements arranged to form flow channels, such as, for example, cellular foam, open-cell foam, porous tissue collections, liquids, gels, and foams that include, or cure to include, flow channels. In one embodiment, the manifold 112 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include "closed cells."

Referring still to FIG. 1, the reduced pressure interface 114 may be positioned adjacent to or coupled to the drape 116 to provide fluid access to the manifold 112. The reduced pressure interface 114 may be coupled to the drape 116 by an adhesive 121 similar to the adhesive 120 described above. The conduit 110 and the reduced pressure connector 108 fluidly couple the reduced pressure treatment unit 106 and the reduced pressure interface 114. The reduced pressure interface 114 allows the reduced pressure to be delivered to the tissue site 102. While the amount and nature of reduced pressure applied to the tissue site 102 will typically vary according to the application, the reduced pressure treatment unit 106 will typically provide reduced pressure between −5 mm Hg and −500 mm Hg and more typically between −100 mm Hg and −300 mm Hg.

The reduced pressure treatment unit 106 may include a canister 122 for collecting exudate and a sensing unit 130 in fluid communication with a reduced pressure source 124. While FIG. 1 illustrates that the reduced pressure treatment unit 106 houses the canister 122, the sensing unit 130, and the reduced pressure source 124 in a single housing unit, it should be appreciated that elements of the reduced pressure treatment unit 106, which may include the canister 122, the sensing unit 130, and the reduced pressure source 124, may be located in a number of different housing units that are fluidly connected (not shown). The canister 122 will be discussed in more detail below.

The conduit 110 may be a multi-lumen conduit or tube that provides a continuous conduit between the reduced pressure interface 114 and the reduced pressure connector 108 positioned on the reduced pressure treatment unit 106. While the conduit 110 illustrates multiple lumens, it should be appreciated that the reduced pressure treatment system 100 may operate using a single lumen tube. The conduit 110 may include conduits for carrying reduced pressure and removing liquids alone or may be combined with one or more lumens for sensing pressure and providing a vent or a purging capability. The conduit 110 may include a main lumen 126 and one or more ancillary lumens 128 and is adapted to maintain fluid isolation between the main lumen 126 and the one or more ancillary lumens 128. Liquids or exudate communicated from the manifold 112 through the main lumen 126 are removed from the conduit 110 and retained within the canister 122. The one or more ancillary lumens 128 fluidly communicate reduced pressure levels from the tissue site 102 to the sensing unit 130.

In the embodiment illustrated in FIG. 1, the reduced pressure source 124 is an electrically-driven vacuum pump. In another implementation, the reduced pressure source 124 may instead be a manually-actuated or manually-charged pump that does not require electrical power. The reduced pressure source 124 instead may be any other type of reduced pressure pump, or alternatively a wall suction port such as those available in hospitals and other medical facilities. The reduced pressure source 124 may be housed within or used in conjunction with the reduced pressure treatment unit 106, which may also contain sensors, processing units, alarm indicators, memory, databases, software, display units, and user interfaces 132 that further facilitate the application of reduced pressure treatment to the tissue site 102. In one example, pressure-detection sensors (not shown) located in the sensing unit 130 may be disposed at or near the reduced pressure source 124. The pressure-detection sensors may receive pressure data from the reduced pressure interface 114 via the one or more ancillary lumens 128 that are dedicated to delivering reduced pressure data to the pressure-detection sensors. The pressure-detection sensors may communicate with a processing unit that monitors and controls the reduced pressure that is delivered by the reduced pressure source 124.

Referring now primarily to FIGS. 2-7, but still with reference to FIG. 1, the canister 122 will be described in more detail. The canister 122 is adapted to function in a number of different orientations, and, thus, the canister 122 may be referred to as a multi-orientation canister. The canister 122, however, will generally have a primary operating orientation that will maximize the canister's 122 operational capacity during reduced pressure tissue treatments. Maximizing the canister's 122 operational capacity includes maximizing the life span of any filters used in the canister 122, reducing or eliminating false canister-full alarms, and maximizing the canister's 122 volumetric capacity for exudate storage.

The canister 122 is defined by one or more canister walls 134 arranged to create an enclosure 136. The one or more canister walls 134 may generally define the exterior of the canister 122. The canister 122 includes an inlet 138, a main chamber 140, a filter chamber 142, and an outlet 144. In one embodiment, the canister 122 is in its primary operating orientation when the inlet 138 is generally positioned superior to the main chamber 140 and the filter chamber 142.

The canister 122 may be formed in a number of different ways and from a number of different materials. As illustrated, with particular clarity in the exploded view of FIGS. 3 and 4, the canister 122 may be formed or assembled by joining a main body 162 with a back face plate 164. In one embodiment, the main body 162 and the back face plate 164 may be joined by a tongue-and-groove fitting. In another embodiment, the main body 162 and the back face plate 164 may be joined by and adhesive. Pre-assembled, the main body 162 may have a number of recesses, such as recesses 166 and 168. Likewise, the back face plate 164 may have number of protrusions, such as protrusions 170 and 172. When assembled, the recesses 166 and 168 may receive the protrusions 170 and 172, respectively. In this embodiment, the joining of the recesses 166, 168 with the protrusions 170, 172 define the main chamber 140 and the filter chamber 142. The joining may further define one or more apertures that provide fluid communication between the main chamber 140 and the filter chamber 142. It should be appreciated, however, that other configurations may be available. For example, in one embodiment (not shown), the main body 162 may have interior walls that are preformed to define the perimeters of the main chamber 140 and the filter chamber 142. The interior walls may further include preformed apertures that provide fluid communication between the main chamber 140 and the filter chamber 142. In this embodiment, the back face plate 164 does not include any protrusions that function to substantively join with the main body 162 to form the interior walls that define the main chamber 140 and the filter chamber 142.

Referring again primarily to FIGS. 2-7, the inlet 138 is fluidly connected with the tissue site 102 and is capable of receiving exudate from the tissue site 102. The main chamber 140 is in fluid communication with the inlet 138 and is adapted to receive exudate from the inlet 138. In one embodiment, the canister 122 may further include a receiving chamber 146 positioned between the inlet 138 and the main chamber 140. The receiving chamber 146 may be configured so as to inhibit exudate from splashing when the exudate is transferred from the inlet 138 to the main chamber 140. In another embodiment, a baffle (not shown) may be positioned adjacent the inlet 138 to inhibit the splashing of exudate as the exudate enters the canister 122 through the inlet 138. In yet another embodiment, a baffle may be positioned adjacent the receiving chamber 146 to provide an additional mechanism to reduced exudate splash. The receiving chamber 146 includes an aperture 148 for providing fluid communication between the receiving chamber 146 and the main chamber 140.

The main chamber 140 receives fluids from the inlet 138. A gelling agent (not shown) may be positioned within the main chamber 140. The gelling agent may form a gel upon contact with exudate received from the tissue site 102. The gel formed from the combination of the gelling agent and the exudate may help prevent the exudate from splashing around within the canister 122 when the canister 122 is moved.

The filter chamber 142 is separated from the main chamber 140 by one or more filter chamber walls 150 or partitions. The recesses 166, 168 of the main body 162 may join with the protrusions 170, 172 of the back face plate 164 to form the one or more filter chamber walls 150. The filter chamber walls 150 fluidly separate the main chamber 140 from the filter chamber 142. In one embodiment, the filter chamber 142 is defined by at least a first filter chamber wall 156 and a second filter chamber wall 158. In this embodiment, the recess 166 may join with the protrusion 170 to form the first filter chamber wall 156, and the recess 168 may join with the protrusion 172 to form the second filter chamber wall 158. The first filter chamber wall 156 may be substantially normal to the second filter chamber wall 158. The one or more filter chamber walls 150 may intersect with a centroid 160 of the canister 122. The "centroid" referred to herein is the geometric enter of the canister's 122 three-dimensional shape based on an average of all points on the canister 122. The geometric center may coincide with the canister's 122 center of mass, however, the geometric center is not required to coincide with the center of mass. In a specific, non-limiting embodiment, the first filter chamber wall 156 may intersect the centroid 160 of the canister 122.

Referring still primarily to FIGS. 2-7, the one or more filter chamber walls 150 may include or define a first aperture 152 and a second aperture 154. The first and second apertures 152, 154 may be formed in a number of different shapes. In specific, non-limiting examples, the first and second apertures 152, 154 may be round or square. The first aperture 152 may be formed through the first filter chamber wall 156 and the second aperture 154 may be formed through the second filter chamber wall 158. The first aperture 152 is a distance, D, from the second aperture 154 in three-dimensional space. The first aperture 152 is configured to provide a first path of fluid communication between the main chamber 140 and the filter chamber 142. The second aperture 154 is configured to provide another path of fluid communication between the main chamber 140 and the filter chamber 142. In one embodiment, the first aperture 152 is configured to provide the primary path of fluid communication between the main chamber 140 and the filter chamber 142. The first aperture 152 is a first size and the second aperture 154 is a second size. In one embodiment, the first aperture 152 is larger than the second aperture 154. In another embodiment, the first aperture 152 is the same size as the second aperture 154. In one embodiment, the size of the first and second apertures 152, 154 are configured to prevent fluid, upon entering the main chamber 140, from inadvertently splashing or contacting the interior of the filter chamber 142. In another embodiment, the size of the first and second apertures 152, 154, are configured to prevent gel from entering the filter chamber 142 due to splashing or sloshing.

The first aperture 152 may be positioned on or adjacent the canister's 122 centroid 160. The first aperture 152 may be positioned through the first filter chamber wall 156 in a location that is not adjacent to the one or more canister walls 134 that define the exterior of the canister 122 to inhibit exudate from entering the first aperture 152 as a result of exudate sloshing or splashing. In other words, the first aperture 152 may be spaced apart from the one or more canister walls 134. The second aperture 154 may be positioned through the second filter chamber wall 158 in a location that maximizes the distance between the first aperture 152 and the second aperture 154. In another embodiment, the second aperture 154 may be positioned through the second filter chamber wall 158 as close to the top of the main chamber 140 as possible when the canister 122 is viewed in its primary operating orientation.

As shown, the outlet 144 is positioned adjacent the filter chamber 142 through the one or more canister walls 134. The outlet 144 is adapted to provide fluid communication between the reduced pressure source 124 and the filter chamber 142. A filter (not shown) is positioned within the filter chamber 142. The filter will typically be a hydrophobic filter to prevent exudate and liquids from exiting the canister 122 and reaching the reduced pressure source 124. In addition to a filter, a liquid-air separator (not shown) may be placed between the filter and the reduced pressure source 124 for additional protection of the reduced pressure source 124.

In operation, the reduced pressure source 124 supplies reduced pressure to the tissue site 102 via a fluid communication path linking the reduced pressure source 124 and the tissue site 102. As described above, the manifold 112, the reduced pressure interface 114, the conduit 110, and the canister 122 are all part of the fluid communication path linking the reduced pressure source 124 to the tissue site 102. As reduced pressure is supplied to the tissue site 102, exudate, including liquids, is removed from the tissue site 102 and deposited within the canister 122 for storage. The exudate is first deposited in the main chamber 140 of the canister 122.

The reduced pressure is supplied to the canister 122 via the outlet 144 that is in fluid communication with the filter chamber 142. The filter chamber 142 is in fluid communication with the main chamber 140 by means of the first aperture 152 and the second aperture 154. The second aperture 154 may be significantly smaller than the first aperture 152 such that the first aperture 152 is generally the path of least resistance for fluid communication between the filter chamber 142 and the main chamber 140. In the canister's 122 primary operating orientation, the second aperture 154 may be above or superior in position to the first aperture 152. In this embodiment, when the canister 122 first begins to fill with exudate, reduced pressure is mainly supplied from the filter chamber 142 to the main chamber 140 by way of the first aperture 152 because the first aperture 152 generally presents the path of least resistance. As the main chamber 140 fills with exudate, the first aperture 152 may become occluded as the fluid level in the main chamber 140 reaches the first aperture 152. The first aperture may be occluded as a result of surface tensions.

If the first aperture 152 becomes occluded or blocked with fluid, the second aperture 154 becomes the path of least resistance between the filter chamber 142 and the main chamber 140. Fluid will continue to fill the main chamber 140 until the fluid level reaches the second aperture 154, occluding or blocking the second aperture 154. In this embodiment, when both the first aperture 152 and the second aperture 154 are blocked by fluid as a result of the main chamber 140 becoming full, the path of least resistance between the filter chamber 142 and the main chamber 140 is again through the first aperture 152. Sufficient pressure is created within the filter chamber 142 to cause the fluid in the main chamber 140 to be pulled into the filter chamber 142 though the first aperture 152. Fluid may continue filling the filter chamber 142 until the fluid level in the filter chamber 142 fills, blocking the filter and outlet 144. The configuration of the canister 122 increases the useful life span of the filter by limiting the filter's exposure to exudate before the canister 122 is full. Additionally, the configuration of the canister 122 increases the canister's useful volumetric capacity for storing exudate by filling the main chamber 140 with fluids before the filter chamber 142 is filled with fluids.

In operation, fluids that have entered the filter chamber 142 due to movement of the canister 122 may be removed or drained from the filter chamber 142. Fluids received from the tissue site 102 are deposited into the main chamber 140 of the canister 122. The canister 122 may be moved during operation causing the canister 122 to be rotated into a first position, away from the canister's 122 primary operating orientation. The rotation of the canister 122 may cause fluids in the main chamber 140 to flow into the filter chamber 142 through either the first aperture 152 or the second aperture 154. The second aperture 154 being superior in position to the first aperture 152 when the canister 122 is positioned in its primary operating orientation. If the canister 122 is then rotated back into a second position, substantially aligned with the canister's 122 primary operating orientation, the configuration of the canister 122 in general, and the placement of the apertures 152, 154 specifically, allows fluids in the filter chamber 142 to flow back into the main chamber 140 through the first aperture 152.

In operation, the useful life of the filter positioned in the canister 122 may be extended. Fluids from the tissue site 102 are received into the main chamber 140 of the canister 122. The fluids may react with a gelling agent contained within the main chamber 140 to create a gel. Reduced pressure from the reduced pressure source 124 may be applied to the main chamber 140 via the first aperture 152 until a fluid or gel level in the main chamber 140 covers or reaches the first aperture 152, causing a temporary blockage of the first aperture 152. In response to the first aperture 152 becoming temporarily blocked, reduced pressure is supplied to the main chamber 140 via the second aperture 154 until the fluid or gel level in the main chamber 140 covers or reaches the second aperture 154. The second aperture 154 is superior in position to the first aperture 152 when the canister 122 is positioned in its primary operating orientation. Additionally, the second aperture 154 is significantly smaller is size than the first aperture 152 such that the first aperture 152 generally provides the path of least resistance unless only the first aperture 152 is blocked. In response to the fluid or gel level covering the second aperture 154, reduced pressure is again applied to the main chamber 140 through the first aperture 152 causing the gel in the main chamber 140 to be pulled into the filter chamber 142 until both the main chamber 140 and the filter chamber 142 are substantially full of gel.

During operation of another embodiment, the second aperture 154 is substantially the same size as the first aperture 152. In response to a liquid or gel level covering the first aperture 152, the second aperture 154 becomes the path of least resistance. However, in response to the liquid or gel level covering the second aperture 154, reduced pressure is applied to the main chamber 140 through both the first and second apertures 152, 154 causing the liquid or gel in the main chamber 140 to be pulled into the filter chamber 142 until both the main chamber 140 and the filter chamber 142 are substantially full of liquid or gel.

In one embodiment, the canister 122 is referred to as a liquid-collection canister. The liquid-collection canister includes a first and second chamber fluidly isolated from one another by one or more walls. The first chamber may be a main chamber similar to the main chamber 140 and the second chamber may be a filter chamber similar to the filter chamber 142. A plurality of apertures may be positioned in the one or more walls to provide fluid communication between the first and second chambers. The liquid-collection canister may further include an inlet capable of receiving fluids from a tissue site. The inlet is adapted to provide fluid communication between the tissue site and the first chamber. One aperture of the plurality of apertures may be positioned in a plane perpendicular to another of the plurality of apertures. The one aperture may have a first diameter larger than a second diameter of the another of the plurality of apertures. The one aperture may be positioned below the another aperture in the liquid-collection canister's primary operating orientation. The liquid-collection canister may further include an outlet for providing fluid communication with the second chamber such that the outlet is adapted to be fluidly connected to a reduced pressure source.

It should be apparent from the foregoing that an invention having significant advantages has been provided. While the invention is shown in only a few of its forms, it is not just limited but is susceptible to various changes and modifications without departing from the spirit thereof.

While a number of discrete embodiments have been described, aspects of each embodiment may not be specific to only that embodiment and it is specifically contemplated that features of embodiments may be combined with features of other embodiments.

We claim:

1. A canister for use in a reduced pressure tissue treatment, the canister comprising:
   a main chamber adapted to receive liquid from a tissue site;
   a filter chamber adapted to be fluidly coupled to a reduced pressure source and being isolated from the main chamber by one or more walls;
   a first aperture and a second aperture extending through the one or more walls and adapted to provide fluid communication between the main chamber and the filter chamber, wherein the second aperture is vertical to a force of gravity when the canister is in a primary operating orientation; and
   a filter positioned within the filter chamber.

2. The canister of claim 1, the filter being isolated from the main chamber by the one or more walls.

3. The canister of claim 1, further comprising a gelling agent positioned within the main chamber for creating a gel upon contact with fluids received from the tissue site.

4. The canister of claim 1, wherein the first aperture is positioned beneath the second aperture in the canister's primary operating orientation.

5. The canister of claim 1, wherein the first aperture is horizontal to a force of gravity when the canister is in the primary operating orientation.

6. The canister of claim 1, wherein:
   the first aperture is positioned beneath the second aperture in the canister's primary operating orientation; and
   the first aperture is horizontal to a force of gravity when the canister is in the primary operating orientation.

7. The canister of claim 1, wherein the second aperture is smaller than the first aperture.

8. The canister of claim 1, wherein the first aperture is configured to provide less restrictive fluid communication between the main chamber and the filter chamber than fluid communication through the second aperture.

9. A liquid-collection canister comprising:
   a first chamber and a second chamber fluidly isolated by one or more walls; and
   a plurality of apertures positioned in the one or more walls to provide fluid communication between the first chamber and the second chamber, wherein at least one of the apertures is vertical relative to a force of gravity in a primary operating orientation of the liquid-collection canister.

10. The liquid-collection canister of claim 9, wherein one of the plurality of apertures is located at a centroid of the liquid-collection canister.

11. The liquid-collection canister of claim 9, wherein one aperture of the plurality of apertures positioned in a plane perpendicular to another of the plurality of apertures.

12. The liquid-collection canister of claim 9, wherein one of the plurality of apertures has a first diameter and another of the plurality of apertures has a second diameter smaller than the first diameter.

13. The liquid-collection canister of claim 9, further comprising a filter positioned within the second chamber and isolated from the first chamber by the one or more walls.

14. The liquid-collection canister of claim 9, further comprising a baffle positioned to inhibit splashing of fluids as the fluids enter the liquid-collection canister.

15. The liquid-collection canister of claim 9, further comprising a gelling agent positioned within the first chamber for creating a gel upon contact with fluids received from the tissue site.

16. The liquid-collection canister of claim 9, wherein at least one of the plurality of apertures is positioned beneath another of the plurality of apertures in the liquid-collection canister's primary operating orientation.

17. The liquid-collection canister of claim 9, wherein at least one of the plurality of apertures is horizontal to a force of gravity when the liquid-collection canister is in the primary operating orientation.

18. The liquid-collection canister of claim 9, wherein at least one of the plurality of apertures is configured to provide less restrictive fluid communication between the first chamber and the second chamber than fluid communication through another of the plurality of apertures.

* * * * *